United States Patent
Lu et al.

(10) Patent No.: US 8,029,770 B2
(45) Date of Patent: Oct. 4, 2011

(54) CAFFEINE SALT COMPLEXES AND METHODS FOR USING THE SAME IN THE PREVENTION OR TREATMENT OF CANCER

(75) Inventors: Yaoping Lu, North Brunswick, NJ (US); Allan H. Conney, Princeton, NJ (US); YouRong Lou, North Brunswick, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 197 days.

(21) Appl. No.: 12/393,237

(22) Filed: Feb. 26, 2009

(65) Prior Publication Data

US 2009/0162299 A1 Jun. 25, 2009

Related U.S. Application Data

(63) Continuation of application No. 10/894,614, filed on Jul. 20, 2004, now abandoned.

(60) Provisional application No. 60/488,401, filed on Jul. 21, 2003.

(51) Int. Cl.
*A61K 8/00* (2006.01)
*A61K 39/00* (2006.01)
*A61Q 17/04* (2006.01)

(52) U.S. Cl. ................. 424/60; 424/277.1

(58) Field of Classification Search ............ 424/59, 424/60, 277.1
See application file for complete search history.

(56) References Cited

U.S. PATENT DOCUMENTS

| | | | | | |
|---|---|---|---|---|---|
| 3,919,413 | A | * | 11/1975 | Mebus | 424/221.1 |
| 5,656,278 | A | * | 8/1997 | Enjolras | 424/401 |
| 5,922,331 | A | * | 7/1999 | Mausner | 424/401 |
| 6,316,435 | B2 | | 11/2001 | Byrd et al. | 514/211.08 |
| 6,642,274 | B1 | | 11/2003 | Neal | 514/573 |

FOREIGN PATENT DOCUMENTS

WO WO 98/23165 * 6/1998

OTHER PUBLICATIONS

National Cancer Institute: Breast cancer prevention retrieved online Aug. 20, 2008 via http://www.cancer.gov/cancertopics/pdq/prevention/breast/Patient/page 3.*
Medline Plus : Medical Encyclopedia: Ovarian cancer retrieved online on Aug. 20, 2008 via: https://www.nlm.nih.gov/medlineplus/ovariancancer.html, p. 1 dated on Jul. 31, 2008.*
Zips et al. in vivo, 2005, 19:1-8.*
Lu et al. (Oncol. Res. 2002; 13(2): 61-70).*
Lu et al. (PNAS, 2002: 99(19), p. 12455-12460).*
Fan et al., "Disruption of p53 Function Sensitizes Breast Cancer MCF-7 Cells to Cisplatin and Pentoxifylline", Cancer Research 1995 55:1649-1654.
Huang et al., "Effects of Tea, Decaffeinated Tea, and Caffeine on UVB Light-induced Complete Carcinogenesis in SKH-1 Mice:Demonstration of Caffeine as a Biologically Important Constituent of Tea[1]", Cancer Research 1997 57:2623-2629.
Koniaras et al., "Inhibition of Chk1-dependent G2 DNA damage checkpoint radiosensitizes p53 mutant human cells", Oncogene 2001 20:7453-7463.
Lock et al., "Concentration-dependent Differences in the Mechanisms by Which Caffeine Potentiates Etoposide Cytotoxicity in HeLa Cells[1]", Cancer Research 1994 54:4933-4939.
Lou et al., "Effects of Oral Administration of Tea, Decaffeinated Tea, and Caffeine on the Formation and Growth of Tumors in High-Risk SKH-1 Mice Previously Treated With Ultraviolet B Light", Nutrition and Cancer 1999 33(2):146-153.
Lu et al., "Inhibitory effect of black tea on the growth of established skin tumors in mice:effects on tumor size, apoptosis, mitosis and bromodeoxyuridine incorporation into DNA", Carcinogenesis 1997 18(11):2163-2169.
Lu et al., "Stimulatory Effect of Oral Administration of Green Tea or Caffeine on Ultraviolet Light-induced Increases in Epidermal Wild-Type p53, p21 (WAF1/CIP1), and Apoptotic Sunburn Cells in SKH-1 Mice[1]", Cancer Research 2000 60:4785-4791.
Lu et al., "Topical applications of caffeine or (−)-epigallocatechin gallate (EGCG) inhibit carcinogenesis and selectively increase apoptosis in UVB-induced skin tumors in mice", Proc. Natl. Acad. Sci. USA 2002 99(19):12455-12460.
Lu et al., "Inhibitory Effects of Orally Administered Green Tea, Black Tea, and Caffeine on Skin Carcinogenesis in Mice Previously Treated with Ultraviolet B Light (High-Risk Mice):Relationship to Decreased Tissue Fat[1]", Cancer Research 2001 61:5002-5009.
Lu et al., "Stimulatory Effect of Topical Application of Caffeine on UVB-Induced Apoptosis in Mouse Skin", Oncology Research/Anti-Cancer Drug Design 2002 13:61-70.
Nghiem et al., "ATR inhibition selectively sensitizes $G_1$ checkpoint-deficient cells to lethal premature chromatin condensation", Proc. Natl. Acad. Sci. USA 2001 98(16):9092-9097.
Powell et al., "Differential Sensitivity of $p53^{(-)}$ and $p53^{(+)}$ Cells to Caffeine-induced Radiosensitization and Override of $G_2$ Delay[1]", Cancer Research 1995 55:1643-1648.
Russell et al., "Preferential Radiosensitization of G1 Checkpoint Deficient cells by Methylxanthines", Int. J. Radiation Oncology Biol. Phys. 1996 36(5):1099-1106.
Zajdela et al., "Inhibition of Skin Carcinogenesis In Vivo by Caffeine and Other Agents", Natl. Cancer Inst. Monogr. 1978 50:133-140.

* cited by examiner

*Primary Examiner* — Johann Richter
*Assistant Examiner* — Mei-Ping Chui
(74) *Attorney, Agent, or Firm* — Licata & Tyrrell P.C.

(57) ABSTRACT

The present invention relates to pharmaceutical compositions containing a caffeine salt complex and a pharmaceutically acceptable carrier for use in methods for preventing or treating cancer or solar dermatitis. Methods for inducing apoptosis or inhibiting proliferation in a cancer cell or cell which as UVB-induced DNA damage using a caffeine salt complex or methylated xanthine are also provided.

5 Claims, 2 Drawing Sheets

CAFFEINE SALT COMPLEXES AND METHODS FOR USING THE SAME IN THE PREVENTION OR TREATMENT OF CANCER

This application is a continuation of U.S. application Ser. No. 10/894,614 filed Jul. 20, 2004, now abandoned which claims the benefit of priority from U.S. Provisional Application Ser. No. 60/488,401, filed on Jul. 21, 2003 whose contents are incorporated herein by reference in their entireties.

This invention was made in the course of research sponsored by the National Cancer Institute (Grant No. CA80759). The U.S. government has certain rights in this invention.

BACKGROUND OF THE INVENTION

Over half of all new cancers are skin cancers and its incidence is on the rise due to increased recreational exposure to sunlight and depletion of the ozone layer (American Cancer Society's 2004 Facts & Figures; Nataraj, et al. (1995) *Photochem. Photobiol.* 62:218-230; McKenzie, et al. (1999) *Science* 285:1709-1711). While the use of sunscreens has decreased the risk of skin cancers (Stern, et al. (1986) *Arch. Dermatol.* 122:537-545; Glanz, et al. (2002) *Morbid. Mortal. Wkly. Rep.* 51:1-18), there is a need to identify additional approaches for skin cancer prevention in individuals previously exposed to high-dose levels of sunlight.

Treatment of SKH-1 hairless mice with ultraviolet B (UVB) ($30\ mJ/cm^2$) twice a week for 20 weeks results in mice without tumors but with epidermal hyperplasia and a high risk of developing skin tumors during the next several months in the absence of further UVB treatment (Lou, et al. (1999) *Nutr. Cancer* 33:146-153). This animal model resembles humans who have received high levels of exposure to sunlight early in life with reduced exposure later in life. UVB-pretreated high-risk mice have been used for evaluating the effects of potential chemopreventive agents on skin tumor formation in the absence of further exposure to UVB. Oral administration of green tea, black tea, or caffeine to UVB-pretreated high-risk mice inhibits tumorigenesis, but the decaffeinated teas have little or no activity, and reconstitution of the decaffeinated teas with caffeine restores biological activity (Lou, et al. (1999) *Nutr. Cancer* 33:146-153; Lu, et al. (2001) *Cancer Res.* 61:5002-9; Huang, et al. (1997) *Cancer Res.* 57:2623-9). Further, oral administration of black tea to UVB-pretreated mice with tumors selectively inhibits the growth of the tumors by inhibiting proliferation and stimulating apoptosis in the tumors without affecting normal non-UVB-treated skin (Lu, et al. (1997) *Carcinogenesis* 18:2163-2169). Oral administration of green tea or caffeine for two weeks prior to a single irradiation with UVB also enhances UVB-induced increases in epidermal wild-type p53 and apoptosis in the epidermis of SKH-1 mice (Lu, et al. (2000) *Cancer Res.* 60(17):4785-91). In addition, topical application of caffeine to the skin of SKH-1 mice, immediately after irradiation with UVB, decreases the number of nonmalignant and malignant skin tumors (Lu, et al. (2002) *Proc. Natl. Acad. Sci. USA* 99:12455-60) and enhances apoptosis as evidenced by increases in caspase 3 (active form)-immunoreactive-positive cells and caspase 3 enzyme activity in the epidermis (Lu, et al. (2002) *Oncol. Res.* 13:61-70). Similarly, local application of caffeine and theophylline to Swiss (Carshalton) mice reduces the incidence of skin cancer induced by repeated irradiation with UV light (Zajdela and Latarjet (1978) *Natl. Cancer Inst. Monogr.* (50):133-40).

U.S. Pat. No. 6,642,274 further teaches that caffeine and other methylated xanthines are useful in the prevention and treatment of prostate disorders including benign prostatic hypertrophy and carcinoma of the prostate.

Moreover, U.S. Pat. No. 6,316,435 teaches methods and kits for treating lymphoproliferative diseases in a host including administering to a host pentostatin, at least one alkylating agent and at least one methylated xanthine.

BRIEF DESCRIPTION OF THE DRAWINGS

FIG. 1 shows the effect of topical applications of caffeine sodium benzoate on the growth of UVB-induced skin tumors in tumor-bearing SKH-1 mice. Female SKH-1 mice (7 to 8 weeks old) were treated with $30\ mJ/cm^2$ of UVB twice a week for 20 weeks. The UVB was stopped for 24 weeks. These tumor-bearing animals were divided into 2 groups (19 mice per group). One group was treated topically with 100 mg of DERMABASE™ and another group treated with 100 mg of DERMABASE™ containing 4% caffeine sodium benzoate once a day 5 days a week for 8 weeks. The number (FIG. 1A) and size (FIG. 1B) of the tumors were recorded every 2 weeks.

SUMMARY OF THE INVENTION

It has now been shown that caffeine, a caffeine salt complexes, or a methylated xanthines can function both as a sunscreen and a proapoptotic agent in UVB-damaged cells or tumor cells.

Accordingly, the present invention relates to a pharmaceutical composition composed of a caffeine salt complex and a pharmaceutically acceptable carrier.

In one embodiment, a caffeine salt complex is caffeine sodium benzoate, caffeine triiodide, citrated caffeine, valeriante of caffeine, or caffeine sodium salicylate.

In other embodiments, a pharmaceutical composition containing a caffeine salt complex and a pharmaceutically acceptable carrier is a formulation for topical application in the form of an ointment, cream, lotion, paste, gel, spray, aerosol, oil or patch and can be sunscreen or cosmetic. In particular embodiments, such a topical formulation can further contain a skin penetrant enhancer such water, an alcohol, an alkyl methyl sulfoxide, a pyrrolidone, laurocapram, a surfactant, urea, or N,N-diethyl-m-toluamide; or can contain an analgesic agent comprising aloe vera, benzocaine, dibucaine, diphenhydramine, pramoxine, camphor, menthol, or mixtures thereof. In another embodiment, a pharmaceutical composition containing a caffeine salt complex and a pharmaceutically acceptable carrier is used in a method for preventing or treating a cancer. This method involves administering to a subject having or suspected of having a cancer an effective amount of a composition containing a caffeine salt complex and a pharmaceutically acceptable carrier so that the cancer is prevented or treated.

The present also relates to a method for inducing apoptosis in a cancer cell. This method involves contacting a cancer cell with an effective amount of a caffeine salt complex or select methylated xanthine or a salt complex thereof so that apoptosis is induced in said cell.

The present further relates to a method for inhibiting proliferation of a cancer cell. Such a method involves contacting a cancer cell with an effective amount of a caffeine salt complex so that proliferation of said cell is inhibited.

The present invention further relates to a method for selectively inducing apoptosis in a cell which has UVB-induced DNA damage wherein the method involves contacting a cell having UVB-induced DNA damage with an effective amount of a caffeine salt complex or select methylated xanthine or a salt complex thereof so that apoptosis is selectively induced in said cell.

Further provided is a method for preventing or treating solar dermatitis or radiation dermatitis. This method involves administering to a subject an effective amount of a caffeine salt complex, caffeine, or methylated xanthine, or salt complex thereof to prevent or treat solar dermatitis or radiation dermatitis in the subject.

DETAILED DESCRIPTION OF THE INVENTION

Sunlight-induced skin cancer is the most prevalent cancer in the United States and the incidence of skin cancer is expected to increase because of the depletion of the ozone layer and increased recreational exposure to sunlight. Strategies to prevent these cancers would save lives and have significant social impact. It has been shown that topical applications of caffeine inhibit tumor formation in UVB-pretreated mice, and this treatment with caffeine selectively enhances apoptosis in tumors but not in non-tumor areas of the epidermis (Lu, et al. (2002) supra). Further, oral administration of caffeine (0.36 mg/mL in the drinking water) during the course of UVB treatment (30 mJ/cm$^2$ twice a week) strongly inhibits UVB-induced formation of papillomas, keratoacanthomas and squamous cell carcinomas in SKH-1 mice (Lu, et al. (1997) supra).

Since caffeine was found to be a strong stimulator of apoptosis in the epidermis of UVB-treated SKH-1 mice when given immediately after UVB, the effects of compounds structurally-related to caffeine were analyzed for their ability to promote UVB-induced apoptosis in mouse skin. It was found that 1,3-dimethylxanthine (theophylline) and 1,7-dimethylxanthine (metabolites of caffeine) were as active as caffeine in stimulating UVB-induced apoptosis whereas 3,7-dimethylxanthine (theobromine; another metabolite of caffeine) had little or no activity. Further, 1,3,9-trimethylxanthine was somewhat less active than caffeine, and xanthine, pentoxifylline, 8-chlorocaffeine, and 8-bromocaffeine had little or no activity. In a similar study utilizing acetone:water (90:10) as vehicle, theophylline was somewhat more active than caffeine and caffeine sodium benzoate was substantially more active than caffeine (Table 1). Theobromine and pentoxifylline were about half as active as caffeine. To further analyze the effect of caffeine salt complexes on UVB-induced apoptosis in mouse skin, caffeine, caffeine sodium benzoate, caffeine triiodide, and citrated caffeine were prepared in acetone and applied immediately to SKH-1 mice immediately after UVB exposure. It was found that the caffeine salt complexes were 1.5 to 2 times as active as caffeine alone at increasing apoptotic sunburn cells of SKH-1 mice (Table 1) and this effect was specific for salt complexes of caffeine rather than caffeine in the presence of a salt (Table 2). Moreover, like caffeine, non-UVB-treated cells were unaffected by a caffeine salt complex such as caffeine sodium benzoate (Table 3).

While topical application of caffeine in acetone was effective at inducing apoptotic sunburn cells, the effectiveness of caffeine in DERMABASE™ (a commonly employed oil in water emulsion vehicle for use in humans) was also analyzed. The results of this analysis indicated that caffeine was more effective at enhancing UVB-induced apoptosis when applied to the skin in DERMABASE™ than when applied to the skin in acetone. Further, similar to studies using acetone, a caffeine salt complex such as caffeine sodium benzoate enhanced UVB-induced apoptosis in the epidermis to a greater extent than equimolar amounts of caffeine in DERMABASE™ (Table 4). Topical application of an equimolar amount of sodium benzoate was inactive.

Caffeine- and caffeine salt complex-mediated enhancement of UVB-induced apoptosis in the epidermis was found to be specific for these compounds as commercially available sunblocks did not have this effect of inducing apoptotic sunburn cells in the epidermis of SKH-1 mice (Table 5). Therefore, these compounds are the first compounds shown to exert both a sunscreen effect and a proapoptotic effect in UVB-treated skin.

Cell culture studies indicate that DNA damage activates a wild-type p53-dependent G1 checkpoint and a p53-independent G2 checkpoint. Activation of these checkpoints inhibits cell division and allows time for DNA repair prior to mitosis thereby preventing the propagation of DNA damaged cells. Cell culture studies have also shown that treatment of DNA damaged cells with caffeine overrides the G2 checkpoint thereby preventing cells from arresting in G2, and this effect of caffeine results in attempted replication of the DNA damaged cells that results in cell death (Walters, et al. (1974) Biophys. J. 14:99-118; Rowley, et al. (1984) Radiat. Res. 97:178-185; Zampetti-Bosseler and Scott (1985) Mutat. Res. 143:251-256). The use of G2 checkpoint inhibitors to selectively increase the sensitivity of p53-defective tumor cells to DNA-damaging agents has been suggested (Murray (1992) Nature 359:599-604; Weinert and Lydall (1993) Semin. Cancer Biol. 4:129-140; Nurse (1997) Cell 92:865-867; Roberge, et al. (1998) Cancer Res. 58:5701-5706). The inhibitors do not substantially influence the survival of normal cells exposed to DNA-damaging agents since these cells can activate the G1 checkpoint. However, inhibitors of the G2 checkpoint should selectively increase the killing of p53-defective cells by DNA-damaging agents since these cells have a defective G1 checkpoint. In several studies using paired cell lines differing only in their p53 status, using caffeine or the caffeine analog pentoxifylline in combination with ionizing radiation or cisplatin resulted in enhanced killing of p53-defective cells compared with p53wild-type cells (Fan, et al. (1995) Cancer Res. 55:1649-1654; Powell, et al. (1995) Cancer Res. 55:1643-1648; Russell, et al. (1996) Int. J. Radiat. Oncol. Biol. Phys. 36:1099-1106; Yao, et al. (1996) Nat. Med. 2:1140-1143; Bracey, et al. (1997) Clin. Cancer Res. 3:1371-1381).

It has been demonstrated that DNA damage-induced cell-cycle arrest at the G1 checkpoint is highly dependent on wild-type p53 while the G2 checkpoint is still functioning even in p53-deficient cells (Russell, et al. (1996) supra). Further, it has been shown that caffeine abrogates G2-arrest only in p53-deficient cells in response to irradiation (Powell, et al. (1995) supra). Caffeine specifically abrogates G2-arrest caused by DNA damaging agents and preferentially sensitizes p53-deficient cells to DNA-damaging agents. Pentoxifylline (structure related to caffeine) preferentially sensitizes p53-defective mammary carcinoma cells to cisplatin-induced apoptosis (Fan, et al. (1995) supra). Treatment of p53-inactive Hela cells with caffeine abrogates etoposide-induced G2-arrest and concomitantly enhanced its cytotoxic effects (Russell, et al. (1996) supra; Lock, et al. (1994) *Cancer Res.* 54:4933-4939). In additional studies, caffeine was found to abrogate the G2 checkpoint that was activated by DNA damage in several p53 mutant tumor cell lines (Koniaras, et al. (2001) *Oncogene* 20:7453-7463). Although several cell culture studies indicate that caffeine selectively enhances the toxic effects of DNA damaging agents in p53 deficient cells, the treatment of serum-starved JB6 C141 cells with caffeine enhances apoptosis via a p53- and bax-dependent pathway whereas treatment of a p53-deficient fibroblast cell line with caffeine fails to enhance apoptosis (He, et al. (2003) *Cancer Res.* 63:4396-4401).

As cell culture studies with different cell lines performed under varying experimental conditions (usually with a high concentration of caffeine) have generated conflicting results, in vivo animal studies using clinically achievable concentrations of caffeine were conducted herein. To illustrate, the proapoptotic effects of topical application of caffeine immediately after a single dose of UVB was analyzed using C57BL/6J p53 knockout mice and their wild-type littermates as controls. The time course for apoptosis was determined by utilizing morphologically distinct sunburn cells as the marker for apoptosis. Exposure of shaved C57/BL/6J black p53 wild-type mice to a single dose of 60 mJ/cm$^2$ of UVB resulted in a comparable increase in apoptotic sunburn cells as occurred in SKH-1 hairless mice exposed to 30 mJ/cm$^2$ of UVB, and peak levels of apoptotic sunburn cells were observed at 6-10 hours after UVB treatment. Accordingly, studies with a C57/BL/6J mouse were performed with a 60 mJ/cm$^2$ dose of UVB.

Topical applications of 1.2 mg caffeine in 100 µL acetone to female C57/BL/6J p53(+/+)mice immediately after a single application of UVB and another two applications, 0.5 and 2 hours later, enhanced the formation of UVB-induced apoptotic sunburn cells by 127% at 6 hours after UVB, when compared with the control animals treated with UVB plus acetone vehicle. Topical applications of caffeine to non-UVB-treated mice had no effect on apoptosis.

Exposure of female C57/BL/6J p53(−/−) mice to 60 mJ/cm$^2$ of UVB resulted in only a small increase in apoptotic sunburn cells; however, exposure to 60 mJ/cm$^2$ of UVB, followed immediately by treatment with caffeine resulted in a large increase in apoptotic sunburn cells. Topical application of caffeine to female p53(−/−) mice enhanced the UVB-induced increase in apoptotic sunburn cells by 563% at 6 hours after UVB irradiation. Topical applications of caffeine to male p53(−/−) mice enhanced UVB-induced increase in apoptotic sunburn cells by 207-418% at 6-10 hours after UVB irradiation. Topical applications of caffeine had no effect on apoptosis in non-UVB-treated epidermis in either male p53 (+/+) or male p53(−/−) mice. These results indicate that caffeine application has a selective stimulatory effect on apoptosis in the epidermis of mice treated with UVB. Similar results were also obtained with caspase-3 (active form) as a biomarker for apoptosis, thus indicating that caffeine can enhance UVB-induced apoptosis by a p53-independent mechanism.

The effect of topical application of a caffeine salt complex such as caffeine sodium benzoate on the growth of UVB-induced skin tumors in tumor-bearing SKH-1 mice was also analyzed. SKH-1 mice exposed to UVB twice a week for 20 weeks were subsequently treated with DERMABASE™ or 4% caffeine sodium benzoate in DERMABASE™ and the number and size of tumors that developed in these mice were monitored. A 2-fold reduction in the number of tumors that developed per mouse and a nearly 3-fold reduction in tumor volume per mouse were observed in mice 8 weeks after treatment with caffeine sodium benzoate compared to mice treated with DERMABASE™ (FIG. 1). In a similar study, comparing DERMABASE™, 1.2% and 3.6% caffeine in DERMABASE™, and 2% and 6% caffeine sodium benzoate in DERMABASE™, both concentrations of caffeine sodium benzoate were found to significantly reduce the percent of mice bearing tumors and the number of tumors per mouse (see Table 6).

Figure 2:
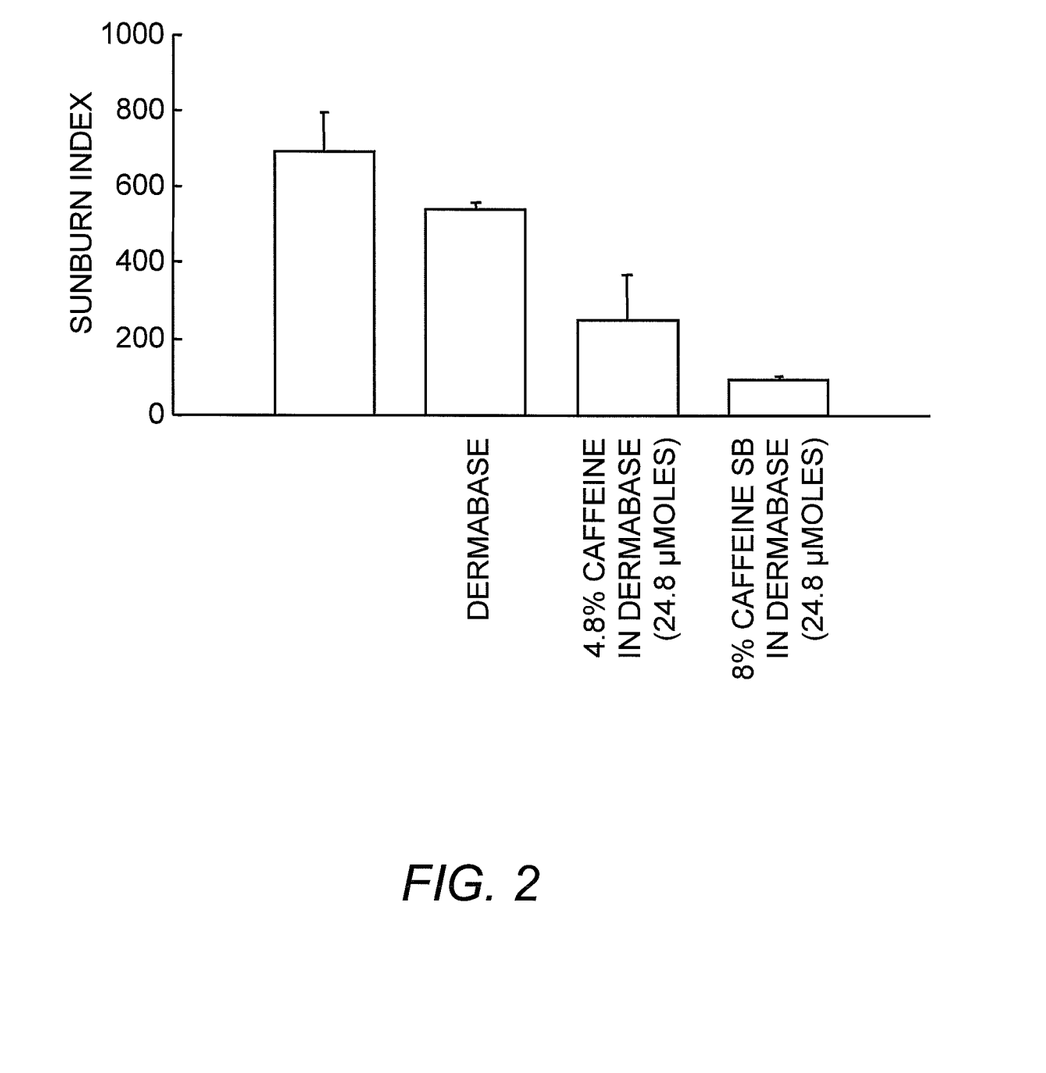
FIG. 2 shows that a caffeine salt complex can prevent the formation of skin lesions in mice exposed to UVB. Female SKH-1 mice (5 mice/group) were treated topically with 100 mg of DERMABASE™, 4.8% caffeine or 8.0% caffeine sodium benzoate in DERMABASE™ 30 minutes before UVB ($180\ mJ/cm^2$), and these treatments were repeated 24 hours later. The areas ($mm^2$) and the intensity of red color in UVB-induced skin lesion were estimated semi-quantitatively 5 days after first UVB treatment. The lesion index were calculated as the lesion area multiplied by the arbitrary intensity: 0, no lesion; 1 barely detectable red lesion; 2 moderate red lesion, and 3, bright red lesion.

To evaluate the proapoptotic effect of caffeine in the absence of a potential confounding sunscreen effect of caffeine, caffeine was routinely applied topically after exposure to UVB. This procedure avoided the potential sunscreen effect of caffeine and demonstrated that application of caffeine enhanced UVB-induced apoptosis. However, for practical purposes, topical applications of a caffeine-containing cream would be either prior to or after sunlight exposure. Thus, the effect of topical applications of caffeine or caffeine sodium benzoate 30 minutes prior to UVB was analyzed. The results indicated that pretreatment of the mice with caffeine in DERMABASE™ just prior to a high dose (180 mJ/cm$^2$) of UVB on two consecutive days inhibited UVB-induced sunburn lesions and the effect of pretreatment with an equimolar amount of caffeine sodium benzoate had an even more dramatic inhibitory effect on the formation of UVB-induced sunburn lesions (FIG. 2). Outdoor occupational human exposure to UVB or a sunbathing exposure in the summer has been reported to range from 50-100 mJ/cm$^2$ per day (Larko, et al. (1983) *Clin. Exp. Dermatol.* 8:279-285; Diffey (1991) *Phys. Med. Biol.* 36:299-328). Thus, the effect of pretreatment with caffeine or caffeine sodium benzoate on the formation of UVB-induced thymine dimers can also be measured as an index of cellular UVB exposure. It is contemplated that pretreatment of mice with caffeine or caffeine sodium benzoate prior to UVB exposure will decrease UVB-induced thymine dimers and increase the ratio of apoptotic cells to thymine dimer-containing cells.

Further, in a similar series of in vitro experiments, treatment of prostate tumor cell line PC-3 with 0.1, 0.2 or 0.5 mM of caffeine sodium benzoate for 96 hours revealed a dose-response relationship on apoptosis. Similar to the results seen with skin cancer cells, the pro-apoptotic effect of caffeine sodium benzoate was more potent than caffeine at all dose levels tested. Moreover, a similar effect has been observed using caffeine sodium benzoate in PANC-1 pancreatic cancer cells.

The results provided herein indicate that a caffeine salt complex, including but not limited to, caffeine sodium benzoate, caffeine triiodide, citrated caffeine, valeriante of caffeine, or caffeine sodium salicylate, is significantly more active than caffeine in stimulating UVB-induced apoptosis and at preventing tumor formation. Accordingly, the present invention relates to the use of a caffeine salt complex to induce apoptosis or inhibit proliferation of a cancer cell thereby preventing or treating said cancer. Additionally, select methylated xanthines, such as theophylline, theobromine, 1,7-dimethylxanthine, 1,3,9-trimethylxanine and pentoxifylline were also shown to induce apoptosis and, in particular, theophylline and 1,7-dimethylxanthine were as or more effective than caffeine alone. Thus, the invention also relates to the use of select methylated xanthines to induce apoptosis in a cancer cell. As used herein, a select methylated xanthine does not include caffeine. As salt complexes of caffeine were found to enhance the proapoptotic activity of caffeine, it is contemplated that a salt complex of a methylated xanthine will also be useful in inducing apoptosis in a cancer cell. Further, it was demonstrated that caffeine and a caffeine salt complex such as caffeine sodium benzoate inhibited the formation of skin lesions in a mouse model of sunburn. Thus, the present invention further relates to the use of a caffeine salt complex, caffeine, or a methylated xanthine or a salt complex thereof for preventing or treating solar dermatitis (i.e., sunburn) in a subject.

In addition to being classified as normal, acid, or basic, salts are categorized as simple salts, double salts, or complex salts. Simple salts, e.g., sodium chloride, contain only one kind of positive ion (other than the hydrogen ion in acid salts). Double salts contain two different positive ions, e.g., the mineral dolomite, or calcium magnesium carbonate. Complex salts, e.g., those disclosed herein, contain a complex ion that does not dissociate in solution. Caffeine salt complexes can be prepared in accordance with well-established methods. For example, a citrate of caffeine can be obtained by dissolving caffeine in chloroform and dissolving citric acid in alcohol, mixing the two solutions, and upon evaporation crystals of caffeine citrate result. Further, caffeine sodium benzoate can be prepared by triturating caffeine with sodium benzoate in the presence of a sufficient quantity of alcohol to generate a smooth paste which can be dried for subsequent use. Likewise, caffeine sodium salicylate can be prepared by triturating caffeine with sodium salicylate in the presence of a sufficient quantity of alcohol to generate a smooth paste which can be dried for subsequent use.

For use in the methods of the present invention, a caffeine salt complex, caffeine or a select methylated xanthine or a salt complex thereof is conveniently used or administered in a composition containing the active agent in combination with a carrier or vehicle. Such compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams & Wilkins: Philadelphia, Pa., 2000.

A carrier, pharmaceutically acceptable carrier, or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in formulations.

Wetting agents, emulsifiers and lubricants, such as sodium lauryl sulfate and magnesium stearate, as well as coloring agents, release agents, coating agents, sweetening, flavoring and perfuming agents, preservatives, flavonoids and antioxidants can also be present in the compositions.

Exemplary antioxidants include, but are not limited to, ascorbyl palmitate, ascorbic acid (vitamin C), vitamin A, vitamin E acetate, α-lipoic acid, especially DL-α-lipoic acid, coenzyme Q10, glutathione, (−)-epigallocatechin-3-gallate, catechin, galangin, rutin, luteolin, morin, fisetin, silymarin, apigenin, gingkolides, hesperitin, cyanidin, citrin, curcuminoid and derivatives thereof which exhibit antioxidant activity. Antioxidant enzymes are further contemplated for use in the composition of the present invention. Such antioxidant enzymes useful in the present invention include superoxide dismutase, catalase, glutathione peroxidase, methionine reductase and equivalents thereof. These antioxidant enzymes can prevent the formation of free radicals or scavenge the formed free radicals to prevent cell damage.

Flavonoids and/or flavonoid derivatives are also contemplated for inclusion in a pharmaceutical composition of the present invention. Exemplary flavonoids and/or flavonoid derivatives include, but are not limited to, quercetin, quercetrin, myricetin, kaempferol and myrecetrin as these compounds also have some anti-inflammatory activity and/or can help stabilize cell membranes in combination with a relatively low toxicity, both of which activities can be beneficial in the treatment of cancer or solar dermatitis. Also, pharmaceutically acceptable salts of these flavonoids and/or flavonoid derivatives may be employed. The particular flavonoid and/or flavonoid derivative included in the composition can be determined by factors such as toxicity, bioavailability, solubility or dispersability, among others.

It is contemplated a pharmaceutical composition of the present invention can contain a caffeine salt complex or methylated xanthine, or salt complex thereof, or a combination thereof. The pharmaceutical composition can further contain caffeine.

A caffeine salt complex or a select methylated xanthine or a salt complex thereof, also referred to herein as the active agent, can be administered locally or systemically via any route including, but not limited to, oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection (e.g., into the liver, into the brain for delivery to the central nervous system) or direct tumor or intralesional injection. The most suitable route in any given case will depend on the nature and severity of the condition being treated and on the nature of the particular compound which is being used. For injection, the carrier will typically be a liquid, such as sterile pyrogen-free water, pyrogen-free phosphate-buffered saline solution, bacteriostatic water, or Cremophor (BASF, Parsippany, N.J.). For other methods of administration, the carrier can be either solid or liquid.

For oral therapeutic administration, the caffeine salt complex or select methylated xanthine or salt complex thereof can be combined with one or more carriers and used in the form of ingestible tablets, buccal tablets, troches, capsules, elixirs, suspensions, syrups, wafers, chewing gums, foods and the like. Such compositions and preparations should contain at least 0.1% of active compound. The percentage of the compound and preparations can, of course, be varied and can conveniently be between about 0.1 to about 100% of the weight of a given unit dosage form. The amount of active agent in such compositions is such that an effective dosage level will be obtained.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. The above listing is merely representative and one skilled in the art could envision other binders, excipients, sweetening agents and the like. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like.

A syrup or elixir can contain the active agent, sucrose or fructose as a sweetening agent, methyl and propylparabens as preservatives, a dye and flavoring such as cherry or orange flavor. Of course, any material used in preparing any unit dosage form should be substantially non-toxic in the amounts employed. In addition, the active compounds can be incorporated into sustained-release preparations and devices including, but not limited to, those relying on osmotic pressures to obtain a desired release profile.

Formulations of the present invention suitable for parenteral administration contain sterile aqueous and non-aqueous injection solutions of the active agent, which preparations are generally isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use. Intravenous use of a caffeine salt complex is well-known in the art. For example, caffeine sodium benzoate has been used intravenously in humans for the treatment of headaches associated with spinal anesthesia (Yucel, et al. (1999) *Reg. Anesth. Pain Med.* 24(1):51-4).

Prolonged absorption of the injectable compositions can be brought about by including in the composition an agent which delays absorption, for example, monostearate salts and gelatin. Moreover, a Grm1 inhibitor or activator can be administered in a time-release formulation, for example in a composition which includes a slow release polymer. The active compounds can be prepared with carriers that protect the agent against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Formulations suitable for topical application to the skin can take the form of an ointment, cream, lotion, paste, gel, spray, aerosol, oil or other pharmaceutical formulation which accomplishes direct contact between the active agent of the composition of the present invention and the skin. Topical formulations can also be prepared which are suitable for collusive therapy.

Formulations in the forms of ointments, creams, lotions and pastes can generally have carriers in the forms of oleaginous bases (e.g., White Petrolatum and White Ointment); absorption bases formed by adding a water-in-oil emulsifying agent to an oleaginous base (e.g., Hydrophilic Petrolatum, AQUABASE, and AQUAPHOR); water-in-oil emulsion bases, prepared by adding water to an absorption base (e.g., HYDROCREAM, EUCERIN, NIVEA, and Cold Cream); oil-in-water emulsion bases (e.g., DERMABASE, UNIBASE, VELVACHOL, and hydrophilic ointment); and water soluble bases (e.g., polyethylene glycol ointment such as PEG 400-600 G or PEG 3350-400 G). Suitable carriers to produce a spray, gel, or aerosol are well-known in the art.

A carrier for topical application can also contain additional ingredients such as other carriers, moisturizers, humectants, emollients, dispersants, radiation blocking compounds, cleansing agents, anti-infective agents (e.g., antibiotics, fungicides, scabicides, or pediculicides), anti-inflammatory agents (e.g., corticosteroids), keratolytics (agents that soften, loosen, and facilitate exfoliation of the squamous cells of the epidermis), as well as other suitable materials that do not have a significant adverse effect on the activity of the topical composition. Additional ingredients can include, for example a sodium acid phosphate moisturizer, witch hazel extract, glycerine humectant, apricot kernal oil emollient, or corn oil dispersant. Other materials which can optionally be included in a topical composition include inositol or B-complex vitamins.

In one embodiment, a topical formulation containing an active agent of the present invention and a pharmaceutically acceptable carrier further contains transdermal or skin penetrant enhancers. Alternatively, the pharmaceutically acceptable carrier is a skin penetrant enhancer. Suitable skin penetrant enhancers include, but are not limited to, solvents such as water, alcohols (e.g., methanol, ethanol, 2-propanol), alkyl methyl sulfoxides (e.g., dimethylsulfoxide, decylmethyl sulfoxide, tetradecyl methyl sulfoxide), pyrrolidones (e.g., 2-pyrrolidone, N-methyl-2-pyrrolidone, N-(2-hydroxyethyl) pyrrolidone), laurocapram (AZONE), and other solvents such as acetone, dimethyl acetamide, dimethyl formamide, tetrahydrofurfuryl alcohol; amphiphiles such as anionic surfactants (e.g., docusate sodium, sodium lauryl sulfate), cationic surfactants (e.g., quaternary ammonium salts), amphoteric surfactants (e.g., lecithins, cephalins, alkylbetamines), nonionic surfactants (mono-, di-, and triglycerides), and other fatty acids and alcohols (e.g., lauryl, cetyl, and stearyl alcohols), sucrose, sorbitan and PEG; urea and N,N-dimethyl-m-toluamide.

Formulations suitable for transdermal administration can be presented as discrete patches adapted to remain in intimate contact with the epidermis of the recipient for a prolonged period of time. There are two basic designs of the patch system that dictate release characteristics of the active agent and patch behavior: (i) matrix or monolithic and (ii) reservoir or membrane. In the matrix system, the inert polymer matrix binds with the active agent and controls its release from the device. In the reservoir system, the polymer matrix does not control release of the active agent. Instead, a rate-controlling membrane present between the drug matrix and the adhesive layer provides the rate-limiting barrier for release of the active agent from the device. It is contemplated that either patch system is suitable for delivery of an active agent disclosed herein. Formulations suitable for transdermal administration can also be delivered by iontophoresis (see, for example, *Pharmaceutical Research* 3 (6):318 (1986)) and typically take the form of an optionally buffered aqueous solution of the compound. Suitable formulations contain citrate or bis\tris buffer (pH 6) or ethanol/water and contain from 0.1 to 0.2 M of the compound.

An active agent can alternatively be formulated for nasal administration or otherwise administered to the lungs of a subject by any suitable means. In particular embodiments, the active agent is administered by an aerosol suspension of respirable particles containing the active agent, which the subject inhales. The respirable particles can be liquid or solid. The term aerosol includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn, et al. (1992) *J. Pharmacol. Toxicol. Methods* 27:143-159. Aerosols of liquid particles containing the active agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles containing the active agent can likewise be produced with any solid particulate medicament aerosol generator, by techniques known in the pharmaceutical art.

Alternatively, one can administer the active agent in a local rather than systemic manner, for example, in a depot or sustained-release formulation.

Further, the present invention provides liposomal formulations of the active agents disclosed herein. The technology for forming liposomal suspensions is well-known in the art. When the active agent is an aqueous-soluble salt, using conventional liposome technology, the same can be incorporated into lipid vesicles. In such an instance, due to the water solubility of the active agent, the active agent will be substantially entrained within the hydrophilic center or core of the liposomes. The lipid layer employed can be of any conventional composition and can either contain cholesterol or can be cholesterol-free. When the active agent of interest is water-insoluble, again employing conventional liposome formation technology, the active agent can be substantially entrained within the hydrophobic lipid bilayer which forms the structure of the liposome. In either instance, the liposomes which are produced can be reduced in size, as through the use of standard sonication and homogenization techniques.

A liposomal formulation containing an active agent disclosed herein, can be lyophilized to produce a lyophilizate which can be reconstituted with a carrier, such as water, to regenerate a liposomal suspension.

In particular embodiments, a caffeine salt complex or methylated xanthine or salt complex thereof is formulated as a sunscreen or sunblock for use before a subject is exposed to sunlight.

A pharmaceutical composition of the present invention can, in addition to a caffeine salt complex or a methylated xanthine or salt complex thereof, contain other targeting agents for enhancing the prevention or treatment of a cancer. Such targeting agents can be administered to a patient simultaneously with, or following, or both simultaneously with and following the administration of the caffeine salt complex or methylated xanthine or salt complex thereof. As used herein, a targeting agent can be a chemotherapy agent, therapeutic agent or a radionucleide used alone or in combination with other targeting agents. Similar to the active agent, the dosing schedule of the targeting agent is dependent on many factors and may be readily determined by the caregiver or clinician. The targeting agents provided herein are well-known in the art and are routinely administered using standard methodologies and treatment regimes.

Chemotherapy and therapeutic targeting agents which can be used in the drug combination of the invention include, cytotoxic agents such as TAXOL, Cytochalasin B, Gramicidin D, Ethidium Bromide, Emetine, Mitomycin, Etoposide, Tenoposide, Vincristine, Vinblastine, Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof. Therapeutic agents include, but are not limited to, antimetabolites (e.g., Methotrexate, 6-Mercaptopurine, 6-Thioguanine, Cytarabine, 5-Fluorouracil, Decarbazine), alkylating agents (e.g., Mechlorethamine, Thiotepa, Chlorambucil, Melphalan, Carmustine (BCNU), Lomustine (CCNU), Cyclophosphamide, Busulfan, Dibromomannitol, Streptozotocin, Mitomycin C, Cis-Dichlorodiamine Platinum (II) (DDP), Cisplatin), anthracyclines (e.g., Daunorubicin (formerly Daunomycin) and Doxorubicin), antibiotics (e.g., Dactinomycin (formerly Actinomycin), Bleomycin, Mithramycin, and Anthramycin (AMC)), anti-mitotic agents (e.g., Vincristine and Vinblastine) and new agents such as Selective Apoptotic Antineoplastic Drugs (SAANDs) such as APTOSYN® (Exisulind).

In a particular embodiment, caffeine or a caffeine salt complex is used in combination with 5-fluorouracil in the treatment of actinic keratosis.

Radiation therapy targeting agents may include external-beam radiotherapy, internal radioactive seed implants (Brachytherapy), and hemi-body radiation. Radiation therapy uses high-energy, ionizing radiation (e.g., gamma rays) to kill cancer cells. Ionizing radiation can be produced by a number of radioactive substances, such as Cobalt (Co-60), Radium (Ra-228), Palladium (Pd-103), Iodine (I-125), Radon (Rn-221), Cesium (Cs-137), Phosphorus (P-32), Gold (Au-198), Iridium (Ir-192), Boron (B-10), Actinium (Ac-225), Ruthenium (Ru-99), Samarium (Sm-153), and Yttrium (Y-90). Radiotherapy can be applied to shrink a tumor that is later removed by surgery, to relieve symptoms, or to destroy malignant cells in a tumor that cannot be removed surgically.

The pharmaceutical composition of the invention can further be administered in combination with agents which relieve side effects of cancer treatment. Such agents can be administered to a patient before, simultaneously with, or following, or before, simultaneously with and following the administration of the pharmaceutical composition. Examples of such agents which relieve side effects of cancer treatment include, Epoetin alfa to relieve symptoms of anemia; cell-protecting agents such as amifostine; and Strontium-89 and Samarium-153 for the relief of cancer-induced bone pain.

Agents for relieving pain can further be included in a pharmaceutical composition of the present invention. Suitable analgesic agents include, but are not limited to, aloe vera, benzocaine, dibucaine, diphenhydramine, pramoxine, camphor (e.g., 0.5 to 3%), or menthol (e.g., 0.1 to 0.2%). Eutectic mixtures of local anesthetics (e.g., lidocaine/prilocaine as found in EMLA cream) are also useful on skin, especially if used with occlusive dressings.

In particular embodiments, the active agent is administered to the subject in an effective amount, as that term is defined herein. Dosages of active agents can be determined by methods known in the art, see, e.g., Remington: The Science and Practice of Pharmacy, Alfonso R. Gennaro, editor, 20th ed. Lippingcott Williams & Wilkins: Philadelphia, Pa., 2000 and can be administered for the prevention (i.e., before detectable signs or symptoms of a cancer are observed) or treatment (i.e., after detectable signs or symptoms of a cancer are observed) of a cancer. The selected effective dosage level will depend upon a variety of factors including the activity of the particular active agent of the present invention employed, whether the active agent is used for prevention or treatment of cancer, the route of administration, the time of administration, the rate of excretion or metabolism of the particular compound being employed, the duration of the treatment, other drugs, compounds and/or materials used in combination with the particular active agent employed, the age, sex, weight, condition, general health and prior medical history of the patient being treated, and like factors well-known in the medical arts.

A physician or veterinarian having ordinary skill in the art can readily determine and prescribe the effective amount of the pharmaceutical composition required for prevention or treatment of cancer in an animal subject such as a human, agriculturally-important animal, pet or zoological animal.

For example, common human doses of caffeine salt complexes and methylated xanthines or salt complexes thereof which can be administered are generally in the range of about 10 mg/day to about 1000 mg/day.

In alternative dosing regimens, the caffeine salt complexes or methylated xanthines or salt complexes thereof can be administered at intervals other than daily, for example once-weekly dosing, twice-weekly dosing, biweekly dosing, and twice-monthly dosing. In such dosing regimens, appropriate multiples of the dosage would be administered. For example, in a once-weekly dosing regimen, a caffeine salt complex or a methylated xanthine or a salt complex thereof would be administered at dosages of 35 mg/week or 700 mg/week in lieu of seven consecutive daily dosages of 5 mg or 100 mg.

One embodiment of the present invention encompasses the use of a caffeine salt complex in a method for preventing or treating a cancer in a subject having or at risk of having a cancer. A subject having or suspected of having a cancer may exhibit one or more of the typical signs or symptoms associated with the disease. For example, a sign or symptom associated with a skin cancer can include, for example, actinic keratosis (also known as a solar keratosis), a scaly or crusty bump that arises on the skin surface and the base may be light or dark, tan, pink, red, or a combination thereof wherein the bump can occasionally itch or produce a pricking or tender sensation and can further become inflamed and surrounded by redness; or a flat lesion with mixtures of deeply pigmented areas and amelanotic foci or a blue-black and raised or dome-shaped lesion. Further, a sign or symptom associated with breast can a lump, an area of thickening, or a dimple in the breast or the less common signs include breast swelling and redness or an enlarged underarm lymph node. General signs or symptoms of a cancer can include, but are not limited to, a tumor, feelings of weakness, and an increased perception of pain. Patients at risk of having a cancer include those with a family member or family history of having a cancer or who have inherited an abnormal cancer gene. Examples, of such inherited cancers are well-established in the art and can be routinely identified in screening assays.

A subject having or at risk of having a cancer is administered an effective amount of a caffeine salt complex to have a beneficial or desired clinical result. As used herein, an effective amount of a caffeine salt complex is an amount sufficient to effect beneficial or desired results, including clinical results, and, as such, an effective amount of a caffeine salt complex is one which includes, but is not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment can also mean prolonging survival as compared to expected survival if not receiving treatment. As will be understood by the skilled artisan, the signs or symptoms of the cancer can vary with the stage of the cancer and the signs or symptoms associated with various stages are well-known to the skilled clinician. See, for example, The American Joint Committee on Cancer Staging Manual, Sixth Edition.

Another embodiment of the present invention is a method for inhibiting proliferation of a cancer cell. The method involves contacting a cancer cell, either in vivo or in vitro, with an effective amount of a caffeine salt complex so that proliferation of said cell is inhibited or reduced. An effective amount of a caffeine salt complex in the context of this method of the invention is an amount which causes a 30%, 40%, 50%, 60%, 70%, 80%, 90%, 95%, 98%, or 100% decrease in cell proliferation when compared to otherwise same conditions wherein the active agent is not present. As one of skill in the art can appreciate, means for determining cell proliferation can vary depending on whether the cell is in vitro or in vivo.

Cell proliferation measurements in vitro can be determined by counting cells before and after the addition of the active agent and comparing the number of cells present after addition of the active agent to similar cells not contacted with the active agent. Similarly, cell proliferation measurements in vivo can be determined by monitoring the size of a tumor before and after contacting cells of the tumor with the active agent.

A further particular desirable embodiment of the present invention encompasses the use of a caffeine salt complex or a methylated xanthine or a salt complex thereof in a method for inducing apoptosis in a cancer cell. The method involves contacting a cancer cell, either in vivo or in vitro, with an effective amount of a caffeine salt complex or a methylated xanthine or a salt complex thereof so that apoptosis in said cell is induced or promoted. An effective amount of a caffeine salt complex or a methylated xanthine or a salt complex thereof in the context of this method of the invention is an amount which causes 5%, 10%, 20%, 30%, 40%, 50%, 60%, 70%, 80%, 90%, 95%, 98%, or 100% cancer cell death when compared to otherwise same conditions wherein the active agent is not present. Measurements of cell death can be performed using methods well-known to those of skill in the art, e.g., measuring a reduction in tumor size, an decrease in cell number or the expression of apoptosis marker proteins (e.g., caspase 3).

Methods for inhibiting proliferation or inducing apoptosis of a cancer are contemplates as being useful in the prevention or treatment of cancer as well as in the study of cancer morphology or in assays for identifying the molecular mechanisms of cancer growth and proliferation.

The methods of the present invention are particularly suitable for cancers or cancer cells including, but not limited to, skin cancer, ovarian cancer, breast cancer, cervical cancer, colorectal cancer, prostate cancer, liver cancer, lung cancer, stomach cancer, bone cancer, and pancreatic cancer. In particular embodiments of the invention, the active agents disclosed herein are useful in cancer or cancer cells deficient in p53.

The invention further relates to method for selectively inducing apoptosis in a cell which has UVB-induced DNA damage by contacting the cell with an effective amount of a caffeine salt complex or select methylated xanthine or a salt complex thereof. As used herein, selective induction of apoptosis is intended to mean that only cells which have UVB-induced DNA damage are killed whereas cells lacking UVB-induced DNA damage are not induced to undergo apoptosis. It is contemplated that this method of the present invention will be useful in the treatment of wrinkles, freckles and aging of skin, all of which arise from exposure to UVB radiation.

Therefore, the active agents of the present invention can advantageously be routinely included as a component of cosmetic compositions (e.g., foundations, daily moisturizers, eye shadows, and the like).

A still further embodiment of the present invention is a method for preventing, reducing or treating solar dermatitis or radiation dermatitis using a caffeine salt complex, caffeine, or methylated xanthine, or salt complex thereof. One common effect of sun exposure and radiation therapy are the conditions called solar dermatitis and radiation dermatitis, respectively, in which the skin in the exposed area begins to look reddened, irritated or burned. Radiation recall dermatitis has been identified as a particularly bad problem for patients receiving a combination of radiation therapy and chemotherapy to treat cancer. The exposed skin in solar and radiation dermatitis can also develop a moist reaction, especially where there are skin folds, and can become very sore. As demonstrated herein, caffeine and a caffeine salt complex such as caffeine sodium benzoate, effectively prevented or reduced solar dermatitis in a mouse model of sunburn. Accordingly, in accordance with this method of the present invention, an effective amount of a caffeine salt complex, caffeine, or methylated xanthine, or salt complex thereof is topically applied to an area of skin prior to, during or after exposure of that area of skin to the sun. In this method, an effective amount of the active agent is applied in the form of a pharmaceutical composition to the skin one or more times daily, as needed.

For prevention or reduction of solar dermatitis, the pharmaceutical composition is generally applied to the skin before exposure to the sun, e.g., at least once thirty minutes before the start of sun exposure or immediately before sun exposure. For each application, it is desirable to apply an amount of the pharmaceutical composition which is sufficient to cover the area of the skin to be exposed to the sun with a thin layer of the composition. The composition should be rubbed into the skin until little or no residue remains on the skin.

In a method for treating or reducing solar dermatitis or radiation dermatitis, an effective amount of the active agent of the invention is applied one or more times daily, as needed, to an area of skin inflicted with solar dermatitis or radiation dermatitis. In the method, a thin layer of the composition is desirably applied to the inflicted area of skin, as needed, and the composition should be rubbed into the skin until little or no residue remains on the skin.

The method of the present invention provides one or more of the beneficial effects reducing, eliminating or decreasing the signs or symptoms of solar dermatitis or radiation dermatitis. In addition, the method of the present invention can provide one or more additional beneficial effects due to one or more of the ingredients contained in the pharmaceutically acceptable carrier as described herein (e.g., antioxidants, bioflavonoids, or pain relievers). The invention is described in greater detail by the following non-limiting examples.

EXAMPLE 1

General Methods

Chemicals and Animals. Acetone (HPLC grade) was obtained from Fisher Scientific (Pittsburgh, Pa.) and caffeine (>99% pure) was obtained from Sigma (St Louis, Mo.). Female SKH-1 hairless mice (6 to 7 weeks old) were purchased from the Charles River Breeding Laboratories, and the animals were kept in an animal facility for at least one week before use at 7 to 8 weeks of age. Mice were given water and PURINA® Laboratory CHOW® 5001 diet from Ralston-Purina (St. Louis, Mo.) ad libitum, and they were kept on a 12-h light/12-h dark cycle. For the analysis conducted herein, 5 mice were used per group.

Treatment of Mice with UVB. The UV lamps used (FS72T12-UVB-HO; National Biological, Twinsburg, Ohio) emitted UVB (280-320 nm; 75-80% of total energy) and UVA (320-375 nm; 20-25% of total energy). There was little or no radiation below 280 nm or above 375 nm. The dose of UVB was quantified with a UVB Spectra 305 dosimeter (Daevlin, Byran, Ohio). The radiation was further calibrated with a model IL-1700 research radiometer/photometer (International Light, Newburyport, Mass.).

Measurement of Tumor Size and Preparation of Skin Sections. Tumor volume was determined by measuring the three-dimensional size (height, length, and width) of each mass. The average of the three measurements was used as the diameter. The radius (r) was determined, and the volume was calculated by: volume=$4\pi r^3/3$.

For histopathology examination and immunohistochemical analysis, the animals were sacrificed and the dorsal skins were taken to include each of the grossly observed masses in the treated areas of the mice. The skins were stapled flat to a plastic sheet and placed in 10% phosphate-buffered formalin at 4° C. for 24 hours. The skin samples were then dehydrated in ascending concentrations of ethanol (80%, 95%, and 100%), cleared in xylene, and embedded in PARAPLAST (Oxford Labware, St. Louis, Mo.). Four micrometer serial sections of skin were made, deparaffinized, rehydrated with water, and used for regular hematoxylin-eosin (H&E) staining or immunohistochemical staining. The counting and characterization of all tumors was done blinded with respect to treatment group using standard methods (Lou, et al. (1999) *Nutr. Cancer* 33:146-153; Bogovski (1994) in *Pathology of Tumors in Laboratory Animals—Vol II*: for Research on Cancer, Lyon, France), IARC Scientific Publication No. 111, pp. 1-26). All immunohistochemical determinations were made with 400-fold magnification with a light microscope. These examinations were also done blinded with respect to treatment group.

Measurement of apoptotic sunburn cells. Identification of apoptoic sunburn cells was based morphologically on cell shrinkage and nuclear condensation due to fragmentation of the cells. Apoptotic sunburn cells were determined in the epidermis by their intensely eosinophilic cytoplasm and small, dense nuclei, which were observed in H&E-stained histological sections of the skin using light microscopy. The percentage of apoptotic sunburn cells in the epidermis (basal plus suprabasal layers) was calculated from the number of these cells per 100 cells counted from the entire 20 mm length of epidermis for each skin section.

Caspase 3 Immunostaining. Affinity-purified polyclonal rabbit antibody that reacts with the mouse p20 subunit of caspase 3, but does not react with the precursor form, was purchased from R&D Systems (Minneapolis, Minn.). Skin sections used for the measurement of caspase 3 were stained by a horseradish peroxidase-conjugated-avidin method with some modification. Endogenous peroxidase was blocked by incubating the tissue sections in 3% hydrogen peroxide in methanol for 30 minutes at room temperature. Sections were then treated with 0.01 M sodium citrate buffer (pH 6.0) in a microwave oven at high temperature for 10 minutes. The sections were incubated with a protein block (normal goat serum) for 10 minutes, followed by avidin D for 15 minutes and biotin blocking solution for 15 minutes (Avidin-Biotin blocking kit from Vector Laboratories, Burlingame, Calif.) at room temperature. The sections were incubated with caspase 3 primary antibody (1:2000 dilution) for 30 minutes at room temperature followed by incubation with a biotinylated anti-rabbit secondary antibody for 30 minutes and incubation with conjugated-avidin solution (ABC Elite kit; Vector Laboratories) for 30 minutes. Color development was achieved by incubation with 0.02% 3,3'-diaminobenzidine tetrahydrochloride containing 0.02% hydrogen peroxide for 10 minutes at room temperature. The slides were then counterstained with hematoxylin and dehydrated, and coverslips were added for permanent mounting. A positive reaction was shown as a light brown to dark brown precipitate in the cytoplasm and/or perinuclei of the cells. The percent of caspase 3-positive cells was determined in each lesion. In non-tumor areas, the scoring was performed at least 0.5 cm away from tumors.

EXAMPLE 2

Effects of Topical Application of Caffeine Salt Complexes and Methylated Xanthines on Apoptosis Female SKH-1 mice were treated topically with acetone (100 µL), caffeine (1.2 mg; 6.2 µmole) or methylated xanthines or caffeine salt complexes (6.2 µmole) in 100 µL acetone right after a single dose of 30 mJ/cm$^2$ of UVB. Another two applications were at 30 and 120 minutes after UVB. Six hours after UVB, the animals were sacrificed and apoptotic sunburn cells in the epidermis were determined morphologically. As is known in the art, treatment of SKH-1 mice with acetone in the absence of UVB treatment has 0.02% apoptotic sunburn cells in the skin epidermis. The results of topical application of caffeine salt complexes and methylated xanthines on UV-induced increase in apoptotic sunburn cells in the epidermis of SKH-1 mice is shown in Table 1.

TABLE 1

| | Percent Apoptotic Sunburn Cells | | |
|---|---|---|---|
| Treatment | Placebo | Caffeine | % Induction |
| Acetone (100 µL) | — | 0.204 ± 0.040 | — |
| Caffeine (1.2 mg/acetone) | — | 0.506 ± 0.013$^a$ | 148 |
| Caffeine Sodium Benzoate | — | 1.089 ± 0.080$^a$ | 434 |
| Caffeine Triiodide | — | 0.789 ± 0.150$^a$ | 287 |
| Caffeine Citrated | — | 0.757 ± 0.199$^b$ | 271 |
| Theophylline (1,3) | — | 0.703 ± 0.171$^b$ | 245 |
| Theobromine (3,7) | — | 0.358 ± 0.064 | 75 |
| Pentoxifylline (1-R,3,7) | — | 0.318 ± 0.068 | 56 |
| Xanthine | — | 0.221 ± 0.046 | 8 |

Each value represents the mean ± S.E.
Statistically different from the acetone group:
$^a$p < 0.01;
$^b$P < 0.05.

EXAMPLE 3

Specificity of Caffeine Salt Complexes for Inducing Apoptosis

To determine whether the UV-induced increase in apoptitic sunburn cells in the epidermis of SKH-1 mice was a result of the caffeine in the presence of a salt or was specific for a caffeine salt complex, caffeine, caffeine+sodium benzoate salt and caffeine sodium benzoate complex were tested for promoting UV-induced apoptotic sunburn cells in SKH-1 mice.

Female SKH-1 mice were treated topically with 100 µL of acetone:water (9:1), 6.2 µmole (1.2 mg) caffeine, 6.2 µmole (0.9 mg) sodium benzoate, 6.2 µmole (1.2 mg) caffeine plus 6.2 µmole (0.9 mg) sodium benzoate or 6.2 µmole (2.1 mg) caffeine sodium benzoate in 100 µL of acetone:water (9:1) immediately after a single dose of UVB (30 mJ/cm$^2$) and again at 30 and 120 minutes. Six hours after UVB, the animals were sacrificed and apoptotic sunburn cells in the epidermis were determined morphologically. The results of topical applications of caffeine, sodium benzoate or caffeine sodium benzoate on UVB-induced apoptotic sunburn cells in the epidermis of SKH-1 mice are shown in Table 2.

TABLE 2

| | Percent Sunburn Cells | |
|---|---|---|
| Treatment | UVB | % Induction |
| Acetone | 0.21 ± 0.06 | — |
| Caffeine in acetone (6.2 µmole) | 0.64 ± 0.15 | 205 |
| Sodium benzoate (6.2 µmole) | 0.27 ± 0.08 | 29 |
| Caffeine + sodium benzoate (6.2 µmole/each) | 0.69 ± 0.20 | 229 |
| Caffeine sodium benzoate (6.2 µmole) | 1.10 ± 0.10 | 381 |

Each value represents the mean ± S.E.

EXAMPLE 4

Effect of Topical Application of Caffeine Sodium Benzoate in Various Formulations on Apoptosis Acetone Formulation. Female SKH-1 mice were treated topically with 100 µL acetone:water (9:1), caffeine (6.2 µmole) or caffeine sodium benzoate (3.1 or 6.2 µmole) formulated with 100 µL acetone:water (9:1) right after a single dose of 30 mJ/cm$^2$ of UVB. Two additional applications were at 30 and 120 minutes after UVB exposure. Six hours after UVB, the animals were sacrificed and apoptotic sunburn cells in the epidermis were determined morphologically. The results of two separate experiments using topical application of caffeine or caffeine sodium benzoate (SB) in acetone on UV-induced apoptotic sunburn cells in the epidermis of SKH-1 mice are shown in Table 3.

TABLE 3

| | Percent Apoptotic Sunburn Cells | | |
|---|---|---|---|
| Treatment | Non-UVB Treated | Caffeine | % Induction |
| Exp-1 | | | |
| Acetone (100 µL) | — | 0.20 ± 0.04 | — |
| Caffeine (6.2 µmole) | — | 0.51 ± 0.01 | 155 |
| Caffeine SB (6.2 µmole) | — | 1.09 ± 0.08 | 445 |
| Exp-2 | | | |
| Acetone (100 µL) | — | 0.21 ± 0.04 | — |
| Caffeine (6.2 µmole) | — | 0.48 ± 0.04 | 129 |
| Caffeine SB (3.1 µmole) | 0.02 ± 0.01 | 0.45 ± 0.07 | 114 |
| Caffeine SB (6.2 µmole) | 0.03 ± 0.01 | 0.68 ± 0.06 | 224 |

Each value represents the mean ± S.E.
$^a$p < 0.01.

DERMABASE™ Formulations. To establish an effective dose of caffeine or caffeine salt complex in DERMABASE™ for use in UVB-induced apoptotic sunburn cells in SKH-1 mice, increasing concentrations of caffeine sodium benzoate were tested in a DERMABASE™ formulation. Specifically, female SKH-1 mice were treated topically with an equal dose of caffeine or caffeine sodium benzoate (CSB) in 100 mg of DERMABASE™ immediately after a single dose (30 mJ/cm²) of UVB. Six hours after UVB the animals were sacrificed and apoptotic sunburn cells in the epidermis were determined morphologically. The results of these experiments are shown in Table 4.

TABLE 4

| | Percent Sunburn Cells | |
|---|---|---|
| Treatment | UVB | % Induction |
| No Treatment | 0.25 ± 0.04 | — |
| DERMABASE ™ | 0.20 ± 0.08 | — |
| 1.0% CSB in DERMABASE ™ | 0.74 ± 0.20$^a$ | 270 |
| 2.0% CSB in DERMABASE ™ | 0.99 ± 0.20$^a$ | 395 |
| 4.0% CSB in DERMABASE ™ | 1.22 ± 0.19$^a$ | 510 |
| 6.0% CSB in DERMABASE ™ | 1.67 ± 0.31$^a$ | 735 |
| 8.0% CSB in DERMABASE ™ | 1.75 ± 0.32$^a$ | 775 |
| 0.6% Caffeine in DERMABASE ™ | 0.40 ± 0.18$^a$ | 100 |
| 1.2% Caffeine in DERMABASE ™ | 0.58 ± 0.12$^a$ | 190 |
| 2.4% Caffeine in DERMABASE ™ | 0.58 ± 0.14$^a$ | 190 |
| 3.6% Caffeine in DERMABASE ™ | 0.82 ± 0.10$^a$ | 270 |
| 4.8% Caffeine in DERMABASE ™ | 0.96 ± 0.13$^a$ | 380 |

Each value represents the mean ± S.E.
$^a$p < 0.01.

EXAMPLE 5

Effects of Topical Application of Commercial Sunblocks on Apoptosis

Female SKH-1 mice were treated topically with 100 mg of DERMABASE™, or a formulation containing 2.4% caffeine (12.4 µmole) or 4.0% caffeine sodium benzoate (12.4 µmole) in 100 mg DERMABASE™; or 100 mg of a formulation containing sunblock lotion-SPF 30, sunblock lotion-SPF 45 or After-sun (NEUTROGENA®) immediately after 30 mJ/cm² of UVB. Six hours after UVB the animals were sacrificed and apoptotic sunburn cells in the epidermis were determined morphologically. The results of topical application of caffeine, caffeine sodium benzoate or commercial sunblocks on UV-induced apoptotic sunburn cells in the epidermis of SKH-1 mice are shown in Table 5.

TABLE 5

| | Percent Sunburn Cells | |
|---|---|---|
| Treatment | UVB | % Induction |
| DERMABASE ™ | 0.51 ± 0.10 | — |
| 2.4% Caffeine | 1.96 ± 0.20$^a$ | 284 |
| 4.0% Caffeine sodium benzoate | 2.33 ± 0.36$^a$ | 357 |
| Sunblock SPF-35 | 0.94 ± 0.30 | 84 |
| Sunblock SPF-45 | 0.52 ± 0.07 | 2 |
| After-sun | 1.16 ± 0.29 | 127 |

Each value represents the mean ± S.E.
$^a$p < 0.01.

EXAMPLE 6

Inhibitory Effect of Caffeine Sodium Benzoate on Tumor Growth in High Risk Mice

Female SKH-1 mice were treated with 30 mJ/cm² of UVB twice a week for 20 weeks. The resulting mice were divided into 7 groups (30 mice per group) and treated topically with: nothing, 100 mg DERMABASE™, 1.2% caffeine, 3.6% caffeine, 2.0% caffeine sodium benzoate, or 6.0% caffeine sodium benzoate in 100 mg DERMABASE™. Animals were treated once a day, 5 days a week, for 11 weeks. The tumor multiplicity and tumor size were recorded every two weeks and the results of these experiments are shown in Table 6.

TABLE 6

| Week | Treatment | Weight of mouse (g) | Percent of mice with tumors | Tumors per mouse |
|---|---|---|---|---|
| 0 | DERMABASE$^a$ | 30.2 ± 0.5 | 0 | 0 |
| | 1.2% CF$^b$ | 30.3 ± 0.5 | 0 | 0 |
| | 3.6% CF$^a$ | 30.5 ± 0.6 | 0 | 0 |
| | 2% CSB$^a$ | 30.5 ± 0.5 | 0 | 0 |
| | 6% CSB$^a$ | 30.4 ± 0.6 | 0 | 0 |
| 5 | DERMABASE$^a$ | 29.6 ± 0.5 | 27.6% | 0.4 ± 0.1 |
| | 1.2% CF$^b$ | 29.6 ± 0.5 | 14.3% | 0.1 ± 0.1 |
| | 3.6% CF$^a$ | 30.0 ± 0.5 | 17.2% | 0.2 ± 0.1 |
| | 2% CSB$^a$ | 30.3 ± 0.4 | 10.3% | 0.2 ± 0.1 |
| | 6% CSB$^a$ | 29.9 ± 0.5 | 3.4% | 0.0 ± 0.0 |
| 7 | DERMABASE$^a$ | 30.2 ± 0.5 | 34.5% | 0.7 ± 0.2 |
| | 1.2% CF$^b$ | 29.5 ± 0.5 | 28.6% | 0.4 ± 0.1 |
| | 3.6% CF$^a$ | 29.6 ± 0.5 | 13.8% | 0.2 ± 0.1 |
| | 2% CSB$^a$ | 30.6 ± 0.4 | 20.7% | 0.4 ± 0.2 |
| | 6% CSB$^a$ | 29.8 ± 0.5 | 17.2% | 0.2 ± 0.1 |
| 9 | DERMABASE$^a$ | 30.8 ± 0.5 | 55.2% | 1.6 ± 0.4 |
| | 1.2% CF$^c$ | 30.0 ± 0.4 | 35.7% | 0.6 ± 0.2 |
| | 3.6% CF$^a$ | 29.8 ± 0.5 | 31.0% | 0.4 ± 0.1 |
| | 2% CSB$^a$ | 30.6 ± 0.4 | 27.6% | 0.5 ± 0.2 |
| | 6% CSB$^c$ | 30.0 ± 0.5 | 20.7% | 0.3 ± 0.1 |
| 11 | DERMABASE$^a$ | 30.8 ± 0.5 | 62.1% | 2.7 ± 0.6 |
| | 1.2% CF$^b$ | 30.0 ± 0.5 | 53.6% | 1.1 ± 0.3 |
| | 3.6% CF$^a$ | 30.1 ± 0.5 | 55.2% | 1.2 ± 0.3 |
| | 2% CSB$^a$ | 30.7 ± 0.5 | 31.0% | 0.9 ± 0.3 |
| | 6% CSB$^d$ | 30.2 ± 0.5 | 31.0% | 0.5 ± 0.2 |

| Week | Treatment | Tumor volume per tumor (mm³) | Tumor volume per mouse (all mice) (mm³) | No. of large tumors (diameter > 5 mm) |
|---|---|---|---|---|
| 0 | DERMABASE$^a$ | 0 | 0 | 0 |
| | 1.2% CF$^b$ | 0 | 0 | 0 |
| | 3.6% CF$^a$ | 0 | 0 | 0 |
| | 2% CSB$^a$ | 0 | 0 | 0 |
| | 6% CSB$^a$ | 0 | 0 | 0 |
| 5 | DERMABASE$^a$ | 0.8 ± 0.3 | 0.3 ± 0.2 | 0 |
| | 1.2% CF$^b$ | 0.5 ± 0.0 | 0.1 ± 0.0 | 0 |
| | 3.6% CF$^a$ | 0.5 ± 0.0 | 0.1 ± 0.0 | 0 |
| | 2% CSB$^a$ | 0.5 ± 0.0 | 0.1 ± 0.1 | 0 |
| | 6% CSB$^a$ | 0.5 ± 0.0 | 0.0 ± 0.0 | 0 |
| 7 | DERMABASE$^a$ | 1.5 ± 0.7 | 1.1 ± 0.6 | 0 |
| | 1.2% CF$^b$ | 1.3 ± 0.5 | 0.4 ± 0.2 | 0 |
| | 3.6% CF$^a$ | 1.3 ± 0.7 | 0.3 ± 0.1 | 0 |
| | 2% CSB$^a$ | 1.5 ± 0.5 | 0.6 ± 0.4 | 0 |
| | 6% CSB$^a$ | 0.5 ± 0.0 | 0.1 ± 0.1 | 0 |
| 9 | DERMABASE$^a$ | 1.5 ± 0.4 | 2.3 ± 0.8 | 0 |
| | 1.2% CF$^c$ | 3.3 ± 1.5 | 2.0 ± 1.0 | 0 |
| | 3.6% CF$^a$ | 1.9 ± 1.1 | 0.8 ± 0.5 | 0 |
| | 2% CSB$^a$ | 1.9 ± 0.9 | 1.0 ± 0.5 | 0 |
| | 6% CSB$^c$ | 0.9 ± 0.4 | 0.3 ± 0.2 | 0 |
| 11 | DERMABASE$^a$ | 2.3 ± 0.6 | 6.0 ± 2.2 | 0 |
| | 1.2% CF$^b$ | 3.5 ± 1.0 | 3.7 ± 1.4 | 0 |
| | 3.6% CF$^a$ | 1.3 ± 0.4 | 1.6 ± 0.6 | 0 |
| | 2% CSB$^a$ | 2.1 ± 0.6 | 1.8 ± 0.2 | 0 |
| | 6% CSB$^d$ | 2.0 ± 0.5 | 1.0 ± 0.4 | 0 |

CF denotes caffeine, CSB denotes caffeine sodium benzoate.
$^a$Number of mice per group is 29/29.
$^b$Number of mice per group is 28/28.
$^c$Number of mice per group is 28/29.
$^d$Number of mice per group is 27/29.

EXAMPLE 7

Figure 1A:
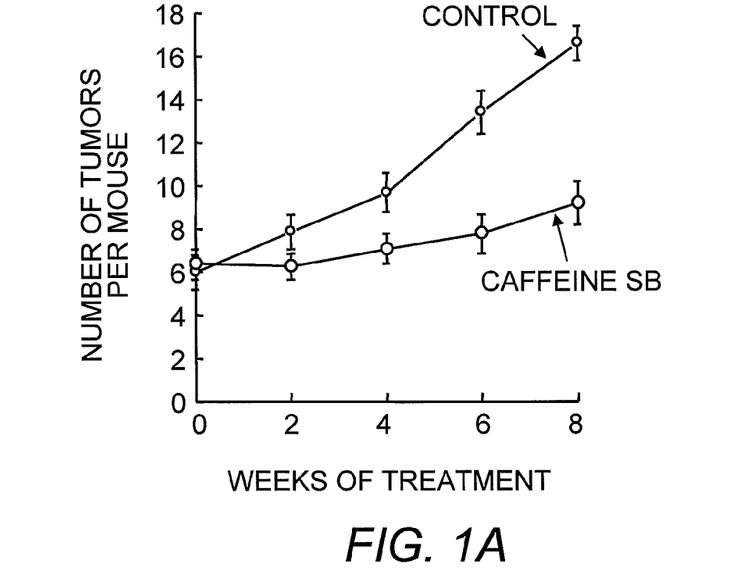
Figure 1B:
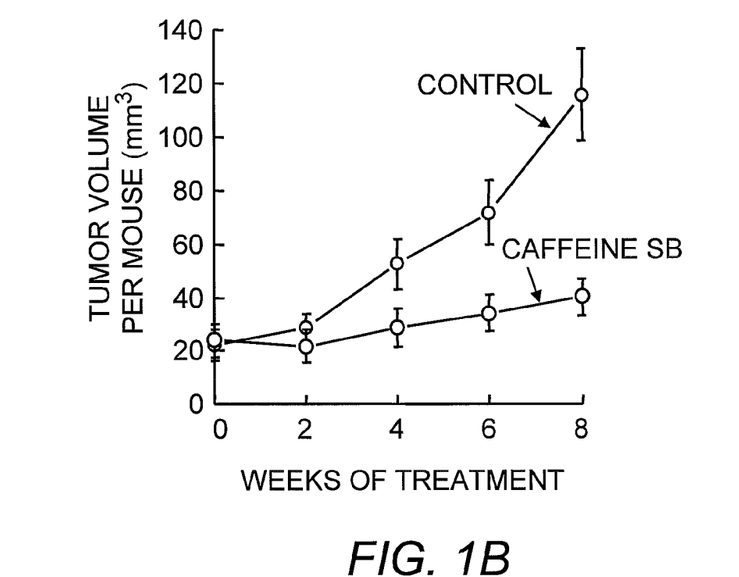

Inhibitory Effect of Caffeine Sodium Benzoate on Tumor Growth in Tumors-Bearing Animals Female SKH-1 mice were treated with 30 mJ/cm$^2$ of UVB twice a week for 20 weeks and UVB were stopped for 24 weeks. The resulting tumor-bearing animals were divided into 2 groups (19 mice per group). One group was treated topically with 100 mg of DERMABASE™ and the other was treated with 100 mg of 4% caffeine sodium benzoate once a day, 5 days a week, for 8 weeks. The number and size of the tumors were recorded every 2 weeks. FIG. 1A and FIG. 1B show that the number and size of tumors are both significantly reduced upon treatment of UVB-exposed mice with caffeine sodium benzoate.

EXAMPLE 8

Prevention of UVB-Induced Skin Lesions Using Caffeine Sodium Benzoate: Sunscreen Effect Female SKH-1 mice were treated topically with 100 mg of DERMABASE™, 4.8% caffeine or 8.0% caffeine sodium benzoate in DERMABASE™ 30 minutes before UVB (180 mJ/cm$^2$) with the treatments repeated 24 hours later. The results of these experiments demonstrate that caffeine sodium benzoate significantly prevented skin lesion formation in mice exposed to UVB irradiation (FIG. 2).

EXAMPLE 9

Mechanisms of UVB-Induced Apoptosis by Caffeine

The mechanisms and molecular targets for the proapoptotic effect of caffeine have been investigated in cultured cell lines. Caffeine-mediated abrogation of DNA damage-induced G2-arrest was initially linked to the activation of cdc2-kinase. Caffeine prevented irradiation-induced inactivation of cdc2 and G2 arrest, and this compound caused apoptosis preferentially in p53-mutated cells (Yao, et al. (1996) supra). ATR has been identified as an important pro-apoptotic target for caffeine in human osteosarcoma cells (Nghiem, et al. (2001) *Proc. Natl. Acad. Sci. USA* 98(16):9092-7), and loss of p53 function sensitized these cells to premature chromatin condensation caused by the ATR inhibitor, caffeine (Nghiem, et al. (2001) supra; Nghiem, et al. (2002) *J. Biol. Chem.* 277:4428-4434). Activation of ATR prevents premature chromatin condensation via Chk1 protein kinase regulation (Nghiem, et al. (2001) supra), and caffeine directly disrupts the checkpoint pathway containing Chk1 (Kumagai, et al. (1998) *J. Cell. Biol.* 142:1559-1569). In addition, ATR protein has higher affinity for DNA in UVB-damaged cells than for undamaged DNA, and damaged DNA stimulates the kinase activity of ATR to a significantly higher level than undamaged DNA (Unsal-Kacmaz, et al. (2002) *Proc. Natl. Acad. Sci. USA* 99:6673-8). Thus, it is contemplated that the ATR/Chk1 signal transduction pathway is an important target for caffeine during its inhibitory effect on UVB-induced skin carcinogenesis.

Although caffeine has been suggested to inhibit the G2 checkpoint by inhibiting ATR-dependent phosphorylation of Chk1 and caffeine has been shown to inhibit ATM and ATR kinase activity in vitro, studies performed with cultured cells unexpectedly indicated that caffeine, in combination with hydroxyurea, stimulates ATR-dependent phosphorylation of Chk1 and Chk2 (Cortez (2003) *J. Biol. Chem.* 278:37139-37145). These results suggest that caffeine may inhibit the ATR/Chk1 signal transduction pathway downstream from the essential ATR-dependent phosphorylation of Chk1 and Chk2. In additional cell culture studies, caffeine was found to activate cdc2 and to abrogate radiation-induced G2 arrest through inhibition of cdc2 phosphorylation on Tyr$^{15}$ and to block the reaction of cdc25c with 14-3-3 (Yao, et al. (1996) supra; Poon, et al. (1997) *Cancer Res.* 57:5168-5178; Qi, et al. (2002) *Radiat. Res.* 157:166-174). Further, treatment of the cultured human ovarian epithelial adenocarcinoma cell line, A2780, with caffeine increases the cytotoxicity of cisplatin and decreases the level of phospho-cyclin B1 (Yazlovitskaya, et al. (2003) *Anticancer Res.* 23:2275-9) which is consistent with an inhibitory effect of caffeine on downstream targets in the ATR/Chk1 signal transduction pathway. It is also possible that caffeine abrogates the G2/M checkpoint by inhibiting the p53-independent p38-mediated signal transduction pathway. A role for p38 at the G2/M checkpoint has been described (Bulavin, et al. (2001) *Nature* 411(6833):102-7).

Moreover, although E2f1 is associated with enhanced apoptosis in certain cell culture systems (Phillips and Vousden (2001) *Apoptosis* 6:173-182; Ginsbert (2002) *FEBS Lett.* 529:122-125; Hsieh, et al. (2001) *Mol. Cell. Biol.* 22:78-93; Nahle, et al. (2002) *Nature Cell Biol.* 4:859-864), a high level of E2f1 is associated with inhibition of UVB-induced apoptosis in mouse skin. It has been demonstrated that E2f1(−/−) knockout mice have enhanced UVB-induced apoptosis in the epidermis when compared with wild-type mice, and the enhanced apoptotic response to UVB was repressed by epidermal-specific overexpression of E2f1 (Wikonkal, et al. (2003) *Nat. Cell Biol.* 5(7):655-60). These results indicate that E2f1 is an inhibitor of UVB-induced apoptosis in mouse skin. Since E2f1 is elevated by DNA damage (possibly through ATM/ATR) (Blattner, et al. (1999) *Mol. Cell. Biol.* 19:3704-3713; Lin, et al. (2001) *Genes Dev.* 15:1833-1844), it is contemplated that caffeine enhances UVB-induced apoptosis by inhibiting the UVB-induced increase in E2f1.

Therefore, the importance of the ATR/Chk1 signaling pathway for the effects of caffeine in animals can be analyzed as can the molecular targets for the selective effects of caffeine on apoptosis that occur in UVB-irradiated skin and in UVB-induced tumors but not in normal epidermis. It is contemplated that the mechanism of the selective stimulatory effect of caffeine on UVB-induced apoptosis in the epidermis is through inhibition of the UVB-activated ATR/Chk1-dependent signal transduction pathway (ATR→Chk1→cdc25c→cdc2→cdc2/cyclin B1). It is further contemplated that skin tumors have an elevated expression of the ATR/Chk1 signal transduction pathway which can be inhibited by caffeine. To illustrate, focal areas of phospho-Chk1 (Ser317)-containing cells were observed in UVB-induced keratoacanthomas and squamous cell carcinomas but not in areas away from the tumors. Further, treatment of UVB-pretreated high-risk mice with caffeine topically 5 days a week for 18 weeks decreased the level of phospho-Chk1 (Ser317) in the tumors.

Further, irradiation of female SKH-1 mice once with UVB (180 mJ/cm2) resulted in increases in the levels of immunologically reactive epidermal ATR, phospho-Chk1 (Ser345), phospho-Chk2 (Ser387), cdc25c, phospho-cdc2 (Tyr15) and phospho-cyclin B1 (Ser147) as measured by western blots using well-known antibodies and immunodetection methods. Irradiation with a low 30 mJ/cm2 dose of UVB resulted in a small decrease in the level of cyclin B1 in the epidermis at 6 hours after UVB, but there was little or no effect on the level of phospho-cyclin B1 (Ser147) as measured by western blot analysis. Topical application of caffeine or caffeine sodium benzoate to a mice immediately after UVB increased substantially the level of epidermal cyclin B1 when compared with the level of epidermal cyclin B1 in mice treated with UVB alone as measured by western blot analysis. In addition, treatment of the mice with UVB (30 mJ/cm2) increased the level of phospho-Chk2 (Ser387) at 6 hours and this effect of UVB was inhibited when the mice were treated topically with caffeine or caffeine sodium benzoate immediately after UVB. In an additional study utilizing frozen sections and an immunohistochemical approach, it was found that topical applications of caffeine or caffeine sodium benzoate to UVB-treated mice substantially enhanced the percent of cyclin B1 positive cells in the epidermis. Treatment of the mice with caffeine or caffeine sodium benzoate in the absence of UVB had little or no effect.

Moreover, irradiation of shaved C57BL/6J p53(−/−) mice and their wild-type p53(+/+) littermates with UVB (60 mJ/cm2) increased the number of phospho-Chk1 (Ser317)-positive cells in the epidermis (measured by immunohistochemical assay), and the response of the p53(−/−) mice to UVB irradiation was greater than the response of the p53(+/+) mice littermates possibly to compensate for the lack of an intact p53-mediated apoptotic pathway. The effect of UVB irradiation on the formation of phospho-Chk1 (Ser296, 317, 345) can also be carried out to evaluate the effect of caffeine administration on UVB-induced changes in phospho-Chk1 and downstream effectors of Chk1.

To study the effect of topical application of caffeine on UVB-induced increase of apoptosis in the epidermis of dominant-negative ATR and Chk1 transgenic mice (on an FVB background) the sensitivity of female and male FVB (ATR/Chk1 wild-type) mice treated with UVB and UVB plus caffeine was evaluated. Shaved female FVB mice (5 mice per group from Charles River Laboratories, Kingston, N.Y.) or male FVB mice (5 mice per group) were treated with 100 μL of acetone or caffeine (1.2 mg; 6.2 μmole) in 100 μL of acetone immediately after UVB (60 mJ/cm2) and at 0.5 and 2 hours later, and the animals were sacrificed 6 hours after exposure to UVB. Apoptotic sunburn cells were identified by changes in morphology and counted.

Topical applications of caffeine to FVB mice enhanced the UVB-induced increase of apoptotic sunburn cells by 120-150%. The sensitivity of this mouse strain to UVB irradiation and caffeine treatment was similar to that of C57BL/6J mice. It is contemplated that dominant-negative ATR and Chk1 transgenic mice (partial inactivation of ATR and Chk1) are more sensitive to the stimulatory effect of UVB on apoptosis than the wild-type mice and that caffeine further enhances UVB-induced apoptosis.

To determine whether topical application of caffeine inhibits the UVB-induced phosphorylation of Chk-1 and/or modify downstream targets in the Chk-1 pathway of G2 arrest, SKH-1 female mice, male p53(−/−) mice, female ATR dominant-negative mice, female dominant-negative Chk1 mice and appropriate wild-type littermate controls are treated with UVB (30 or 60 mJ/cm2) followed immediately by 100 mg DERMABASE™ (control) or 100 mg of 4% caffeine or a caffeine salt complex in DERMABASE™, and the animals are sacrificed at 2, 6, 10, 16, 24 and 48 hours after UVB (5 mice per time interval). Three hundred mice are used, including littermate controls. It is contemplated that the magnitude of the effect of caffeine to enhance UVB-induced apoptosis and to modify the Chk-1 pathway will be greater in p53(−/−) mice than in wild-type mice and that UVB alone and UVB plus caffeine is more effective at enhancing apoptosis in ATR and Chk-1 dominant negative mice (ATR and Chk1 function are partially inhibited) than in their wild-type littermate controls. The effects of caffeine in non-UVB-treated mice are also evaluated and it is contemplated that caffeine is inactive in the absence of UVB.

Further, the effect of topical application of caffeine or control vehicle on the time course for UVB-induced apoptosis in the epidermis of female E2f1(−/−) knockout mice (e.g., 60 mice), female E2f1(−/−):p53(−/−) double knockout mice (e.g., 60 mice) and an equal number of control females is determined. The mice are sacrificed at 2, 6, 10, 16, 24 and 48 hours after irradiation with UVB (30 mJ/cm2; 5 mice/time point), and apoptosis is determined in the epidermis by morphologically distinct apoptotic sunburn cells and caspase 3-positive cells. If E2f1 is a target for caffeine, it is contemplated that topical application of caffeine will enhance UVB-induced apoptosis and inhibit UVB-induced increases in epidermal E2f1 protein in wild-type mice (measured by immunohistochemical assay or by western blot) and that caffeine will not enhance UVB-induced apoptosis in E2f1(−/−):p53(−/−) double knockout mice and possibly not in E2f1(−/−) single knockout mice. Such mice are obtained from Jackson Laboratories (Bar Harbor, Me.) and by matings according to standard methods (Wikonkal, et al. (2003) *Nat. Cell Biol.* 5(7):655-60).

EXAMPLE 10

Prevention of UVB-Induced Formation of Thymine Dimers (Biomarker of UVB Exposure) Using Caffeine or a Caffeine Salt Complex: Sunscreen Effect The effectiveness of oral administration of caffeine or a caffeine salt complex for two weeks before exposure to UVB or topical application of the same shortly before exposure to UVB is determined by measuring the inhibition of the formation of thymine dimers in the epidermis (biomarker of UVB exposure) and enhancement of apoptosis when normalized for the extent of DNA damage.

It was found that topical application of caffeine or caffeine sodium benzoate (24 μmoles) 30 minutes before a high dose of UVB (180 mJ/cm$^2$) on two consecutive days inhibited the formation of sunburn lesions. It is contemplated that this inhibitory effect is caused by a sunscreen effect (caffeine and caffeine sodium benzoate absorb UVB light). Thus, pretreatment of mice with a low dose of caffeine or caffeine sodium benzoate shortly before exposure to UVB will decrease the extent of thymine dimers in epidermal DNA at 0.25 and 0.5 hours after exposure (an index of sunscreen effect and cellular exposure to UVB). It is further contemplated that cells with extensive thymine dimer adducts will be the major cell population that undergoes apoptosis (measured at 6 hours) and that caffeine will enhance apoptosis (sunburn cells) in animals with equivalent DNA damage (thymine dimers).

For studies encompassing topical administration, SKH-1 mice are treated topically with 100 mg of DERMABASE™, 100 mg of 4.8% caffeine in DERMABASE™ (24 μmoles of caffeine) or 100 mg of 8% caffeine sodium benzoate in DERMABASE™ (24 μmoles of caffeine) 30 minutes before exposure to UVB (30 mJ/cm$^2$). The mice are sacrificed immediately before UVB exposure and at 0.25, 0.5 and 6 hours after UVB, and the percent of apoptotic sunburn cells and cells with thymine dimers as well as the intensity of staining for thymine dimers is determined at each time point (e.g., 5 mice per time point; total of 60 mice). The presence of thymine dimers is determined by immunohistochemical methods well-known in the art (Lu, et al. (1999) *Cancer Res.* 59:4591-4602). It is also determined whether UVB-induced apoptotic sunburn cells have more thymine dimers than the nonapoptotic cells by examining the intensity of staining for thymine dimers (antibody catalog No. MC-062; Kamiya Biomedical Co., Seattle, Wash.) in apoptotic sunburn cells vs. the intensity of staining in non-apoptotic cells at 6 hours after exposure to UVB. This analysis is followed by a dose-response study with caffeine and caffeine sodium benzoate (24 µmoles, 12 µmoles, 6 µmoles and 3 µmoles) applied topically in 100 mg of DERMABASE™ or vehicle alone at 30 minutes and 10 minutes before exposure to UVB (30 mJ/cm$^2$). Mice are sacrificed at 0.5 hour and 6 hours after UVB (e.g., 180 mice), and the effect of the pretreatment on UVB-induced thymine dimers and apoptotic sunburn cells is determined.

Subsequently, the effectiveness of topical application of 100 mg DERMABASE™ (vehicle control), or caffeine or caffeine sodium benzoate in 100 mg of DERMABASE™, at different times before irradiation of female SKH-1 mice with UVB, is determined at the level of thymine dimer formation in the epidermis. An optimal dose of caffeine and caffeine sodium benzoate is selected from a dose-response analysis. The level of thymine dimers and apoptotic sunburn cells is determined at 0.5 hour and 6 hours after UVB irradiation. Treatments with caffeine, caffeine sodium benzoate or vehicle are at 8, 4, 2, 0.5 or 0.25 hours before UVB irradiation (e.g., 5 mice/group; 75 mice). Accordingly, it is determined how long the effects of topical applications of caffeine or caffeine sodium benzoate will last. It is contemplated that caffeine and caffeine sodium benzoate will exhibit a sunscreen effect (decrease in UVB-induced thymine dimers) as well as enhanced apoptosis when normalized for DNA damage (extent of thymine dimers). Accordingly, caffeine and caffeine sodium benzoate would exert both a sunscreen effect and a proapoptotic effect in UVB-treated skin.

For studies encompassing oral administration, SKH-1 mice are treated with caffeine (0.4 mg/ml) or a caffeine salt complex in the drinking water for 2 weeks prior to irradiation with UVB (30 mJ/cm$^2$) according to standard methods (Lu, et al. (2000) *Cancer Res.* 60:4785-4791). Control mice receive only water. UVB-induced thymine dimers and apoptotic sunburn cells are measured at 0.25 hour, 0.5 hour, 1 hour, 2 hours, 4 hours, 6 hours, 10 hours, 16 hours, 24 hours and 48 hours after UVB (30 mJ/cm$^2$) (e.g., 110 mice). The mice are treated with UVB at 7 a.m. (end of dark cycle and time of maximum plasma and epidermal levels of caffeine and its metabolites). Subsequently, a dose-response analysis (0, 0.1, 0.2, 0.4, 0.6 mg of caffeine per mL in the drinking water) is conducted for 2 weeks, and plasma and epidermal levels of caffeine are measured at 7 a.m. (e.g., 10 mice/group; 50 mice), and the effects of caffeine to decrease thymine dimers in DNA (at 0.25, 0.5 and 6 hours after UVB) and to enhance apoptosis at 6 hours after UVB are measured (e.g., 65 mice) and compared with human plasma levels of caffeine in heavy coffee drinkers (de Leon, et al. (2003) *Progress Neuro-psychopharma. Biol. Psychia.* 27:165-171). For this analysis, it is determined whether the plasma levels of caffeine and its metabolites that are associated with inhibition of UVB-induced formation of thymine dimers in DNA and enhanced apoptosis in the epidermis of mice are similar or different from the plasma levels of caffeine in coffee drinkers. It is contemplated that caffeine will exhibit a sunscreen-like effect (decreased UVB-induced thymine dimers) and an enhanced ratio of apoptosis (apoptotic sunburn cells) to DNA damage (thymine dimer-containing cells).

EXAMPLE 11

Stimulatory Effect of Topical Application of Caffeine or a Caffeine Salt Complex in Phospho-Chk1 (Ser317)-Positive Foci in UVB-Induced Epidermal Tumors Since most UVB-induced tumors have one or more p53 mutations, the proapoptotic effect of caffeine observed in the epidermal tumors is contemplated as being p53-independent. For example, topical application of caffeine immediately after UVB, enhanced UVB-induced apoptosis in p53(−/−) mice indicating a p53-independent mechanism for the stimulatory effect of caffeine on UVB-induced apoptosis. It is contemplated that high levels of ATR and phosphorylated Chk1 are present in UVB-induced skin tumors due to the presence of DNA damage especially in tumors without functional p53. Immunohistochemical studies indicated foci of multiple cells with phosphorylated Chk1 (Ser317) in many UVB-induced keratoacanthomas and squamous cell carcinomas, which were not observed in the epidermis surrounding the tumors. Unexpectedly, the expression of Chk1 (Ser317) did not occur in all tumor cells but was localized in certain focal areas of the tumors. Treatment of the mice with caffeine for 18 weeks decreased the number of Chk1 (Ser317)-positive cells in keratoacanthomas, but there was little or no effect on the number of positive cells in squamous cell carcinomas. In addition, it was found that treatment of the mice with caffeine decreased the intensity of staining in the Chk1 (Ser317)-positive foci in keratoacanthomas and in squamous cell carcinomas. Therefore, it can be determined whether topical administration of caffeine or caffeine sodium benzoate for 18 weeks (or for 2 weeks) enhances apoptosis in these phospho-Chk1-positive areas of the tumors to a greater extent than in other areas of these tumors. If the phospho-Chk1 positive foci are particularly sensitive to caffeine-induced apoptosis then it can be determined how long it takes for caffeine to exert an apoptotic effect in the Chk1 (317) foci.

It is contemplated that caffeine-induced apoptosis in UVB-induced epidermal tumors is by p53-independent inhibition of the Chk1-dependent pathway leading to apoptosis. Alternatively, or in addition, topical applications of caffeine may enhance apoptosis in tumors by decreasing the level of p38 or E2f1. To evaluate this mechanism, immunohistochemical techniques are employed. For example, it was found that treatment of high risk mice with caffeine topically for 18 weeks decreased the level of phospho-Chk1 (Ser317) in tumors. To further analyze this, UVB-pretreated high risk mice are treated topically with (a) nothing, (b) 100 mg of DERMABASE™, (c) 100 mg of 2.4% caffeine in DERMABASE™ (12.4 µmole caffeine) or (d) 100 mg of 4% caffeine sodium benzoate (12.4 µmol) in DERMABASE™ once a day 5 days a week until the untreated control group or the vehicle-treated control group has 5-8 tumors per mouse (200 mice). The mice are then sacrificed at 2 hours after the last dose of vehicle, caffeine or caffeine sodium benzoate, and skin samples are placed in buffered formalin for 18-24 hours and processed according to standard immunohistochemical methodologies (Lu, et al. (2000) supra; Lu, et al. (2002) *Oncol. Res.* 13:61-70; Lu, et al. (2002) supra). Other samples from an additional 200 animals are frozen, and frozen sections are prepared and used for immunohistochemical assays. In these studies, the effects of caffeine and caffeine sodium benzoate on the number and size of tumors as well as the levels of ATR, phospho-Chk1 (Ser296, 317 and 345), phospho-Chk2 (Thr68), phospho-cdc25c (Ser216), phospho-cdc2, cyclin B1, phospho-cyclin B1 and apoptosis (caspase 3-positive cells) are evaluated in keratoacanthomas, squamous cell carcinomas and in areas of the epidermis away from tumors by using appropriate antibodies. It is contemplated that treatment of the mice with caffeine or caffeine sodium benzoate will inhibit tumor formation and decrease the levels of ATR, phospho-Chk1 (Ser296, 317 and 345), phospho-Chk2 (Thr68) as well as phospho-cdc25c (Ser216), phospho-cdc2 and phospho-cdc2/cyclin B1 in tumors and that non-phosphorylated cyclin B1 and apoptosis (caspase 3-positive cells) will be increased. It is further contemplated that these effects of caffeine and caffeine sodium benzoate will not occur in areas of the epidermis away from tumors.

The effect of caffeine on the p38 kinase signal transduction pathway and E2f1 are also analyzed. The effects of caffeine and caffeine sodium benzoate on the level of p38 and E2f1 in tumors and in areas of the epidermis away from tumors are measured using immunohistochemical assays. Further, the effects of caffeine and caffeine sodium benzoate on the levels of these proteins in freshly harvested tumors and in non-tumor areas of the epidermis are analyzed by immunohistochemistry, western blot analysis, immunoprecipitation and by kinase assays.

What is claimed is:

1. A pharmaceutical composition consisting of a caffeine salt complex and a pharmaceutically acceptable carrier for topical application, wherein said pharmaceutically acceptable carrier is an oil in water emulsion vehicle.

2. The composition of claim 1, wherein the caffeine salt complex is selected from the group consisting of caffeine sodium benzoate, caffeine triiodide, caffeine citrate, caffeine valeriante, and caffeine sodium salicylate.

3. A pharmaceutical composition consisting of caffeine salt complex, an analgesic agent and a pharmaceutical acceptable carrier for topical application, wherein (a) said caffeine salt complex is selected from the group consisting of caffeine sodium benzoate, caffeine triiodide, caffeine citrate, caffeine valeriante, and caffeine sodium salicylate; (b) said pharmaceutically acceptable carrier is an oil in water emulsion vehicle; and (c) said analgesic agent is selected from the group consisting of aloe vera, benzocaine, dibucaine, diphenylhydramine, pramoxine, camphor, and menthol.

4. A method for inducing apoptosis in a skin cancer cell comprising contacting a skin cancer cell with an effective amount of the composition of claim 1 or claim 3 so that apoptosis is induced in said cell.

5. A method for selectively inducing apoptosis in a skin cell which has UVB-induced DNA damage comprising contacting a skin cell having UVB-induced DNA damage with an effective amount of the composition of claim 1 or claim 3 so that apoptosis is selectively induced in said cell.

* * * * *